(12) United States Patent  (10) Patent No.: US 9,149,295 B1
Condon  (45) Date of Patent: Oct. 6, 2015

(54) METHODS AND APPARATUSES FOR SHAPING CARTILAGE FOR TYMPANOPLASTY

(71) Applicant: Kenneth G. Condon, Waukesha, WI (US)

(72) Inventor: Kenneth G. Condon, Waukesha, WI (US)

( * ) Notice: Subject to any disclaimer, the term of this patent is extended or adjusted under 35 U.S.C. 154(b) by 433 days.

(21) Appl. No.: 13/716,596

(22) Filed: Dec. 17, 2012

Related U.S. Application Data

(60) Provisional application No. 61/576,451, filed on Dec. 16, 2011.

(51) Int. Cl.
| | |
|---|---|
| *A61B 17/56* | (2006.01) |
| *A61B 17/16* | (2006.01) |
| *A61B 17/17* | (2006.01) |
| *A61B 17/295* | (2006.01) |

(52) U.S. Cl.
CPC .............. *A61B 17/56* (2013.01); *A61B 17/16* (2013.01); *A61B 17/1604* (2013.01); *A61B 17/1635* (2013.01); *A61B 17/1662* (2013.01); *A61B 17/1679* (2013.01); *A61B 17/17* (2013.01); *A61B 17/1739* (2013.01); *A61B 17/2955* (2013.01); *A61B 2017/1771* (2013.01); *A61B 2017/564* (2013.01)

(58) Field of Classification Search
CPC ............... A61B 17/16; A61B 17/1604; A61B 17/1635; A61B 17/1662; A61B 17/1679; A61B 17/17; A61B 17/1739; A61B 2017/1771; A61B 17/2955; A61B 17/56; A61B 2017/564
See application file for complete search history.

(56) References Cited

U.S. PATENT DOCUMENTS

2003/0216765 A1* 11/2003 Efinger ..................... 606/167

OTHER PUBLICATIONS

Lee et al., Optimal Graft Thickness for Different Sizes of Tympanic Membrane Perforation in Cartilage Myringoplasty: A Finite Element Analysis, Apr. 2007, pp. 725-730.
Webpage, Otology—MicroFrance ENT Instruments, Teixido Cartilage Cutter, Medtronic, Jan. 2013, 2 pages.

* cited by examiner

*Primary Examiner* — Larry E Waggle, Jr.
(74) *Attorney, Agent, or Firm* — Patterson Thuente Pedersen, P.A.

(57) ABSTRACT

A system that harvests cartilage, trims the thickness of the cartilage and shapes the cartilage for reconstruction of the tympanic membrane. The system includes a punch and a template. Punch can include a handle and a plurality of interchangeable cutters having differently shaped cutting portions and a first cutting portion harvests cartilage. Template includes top template and bottom template between which harvested cartilage can be captured to trim the cartilage to a desired thickness. The punch can then be fitted with a second cutter having a desired shape, which is inserted through a pass through recess one of the templates to contact the cartilage to punch out the desired shape in the cartilage.

20 Claims, 8 Drawing Sheets

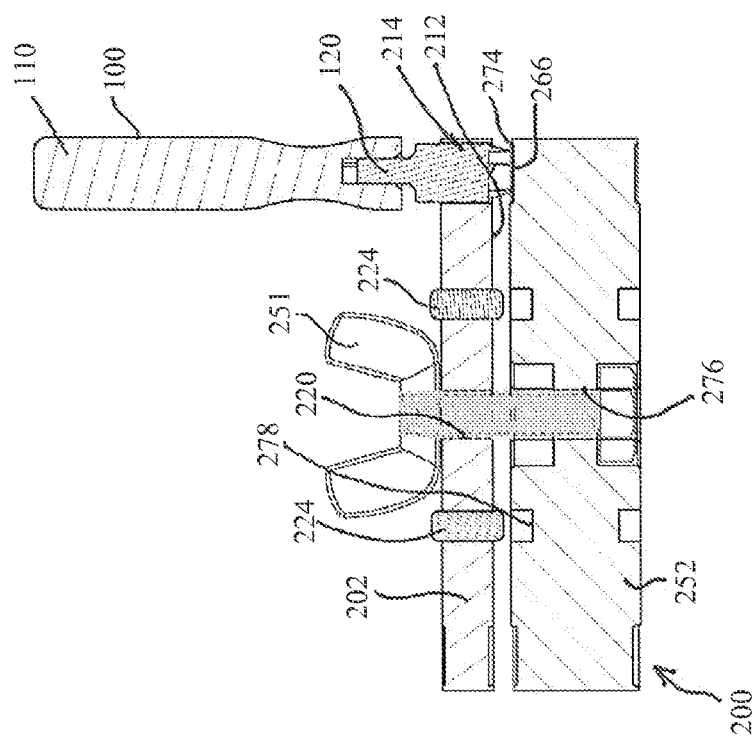
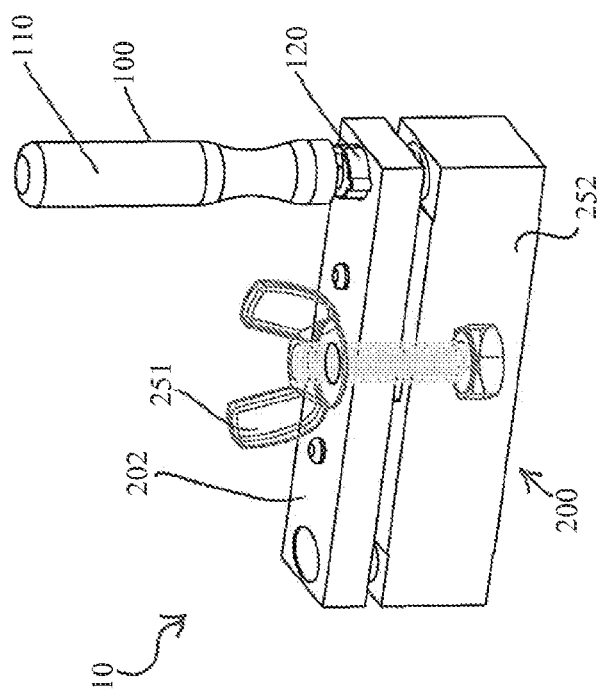

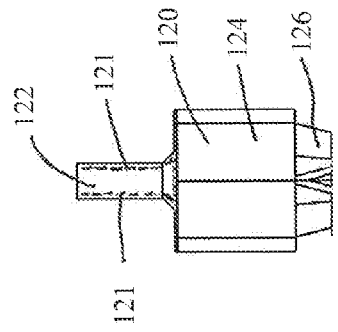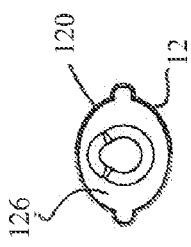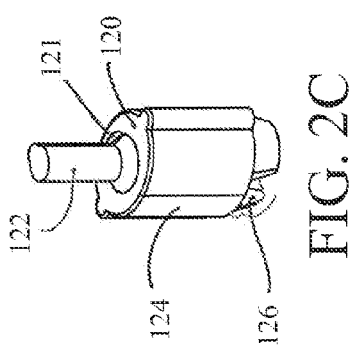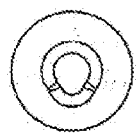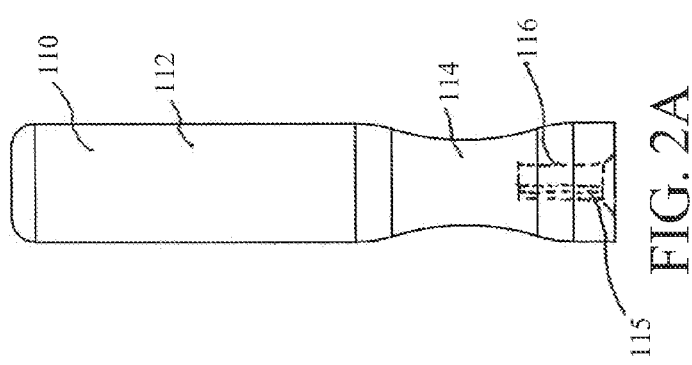

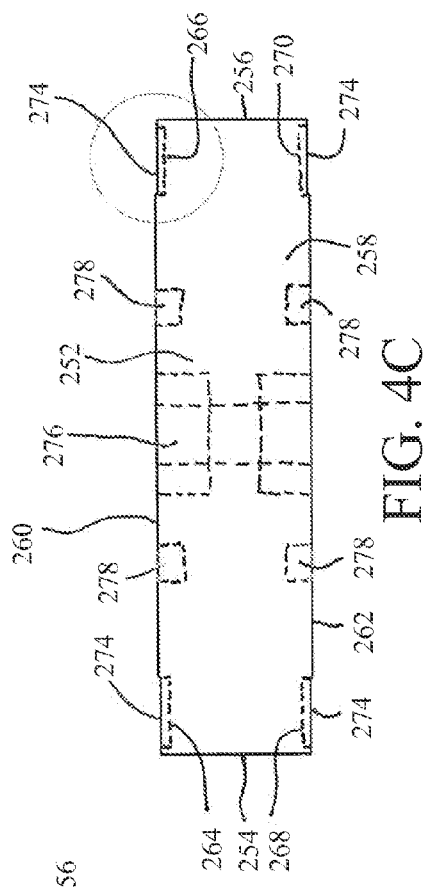
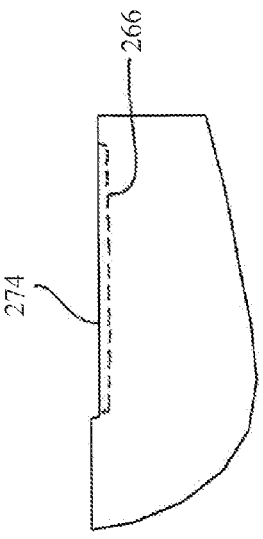
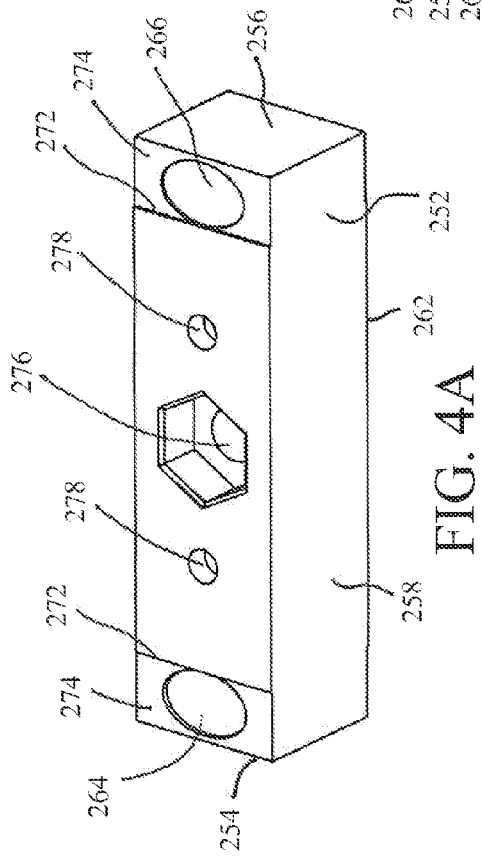
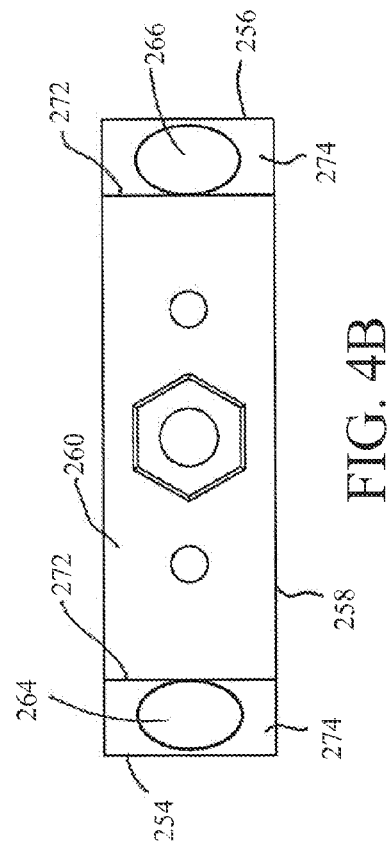

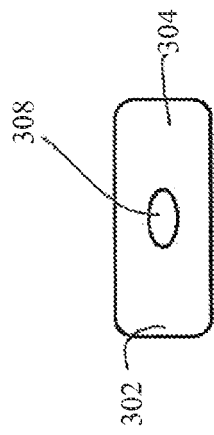
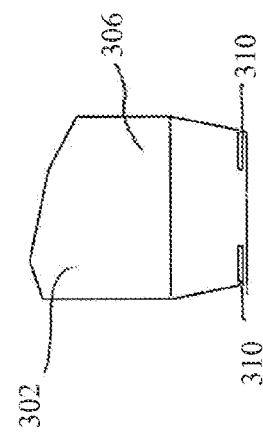
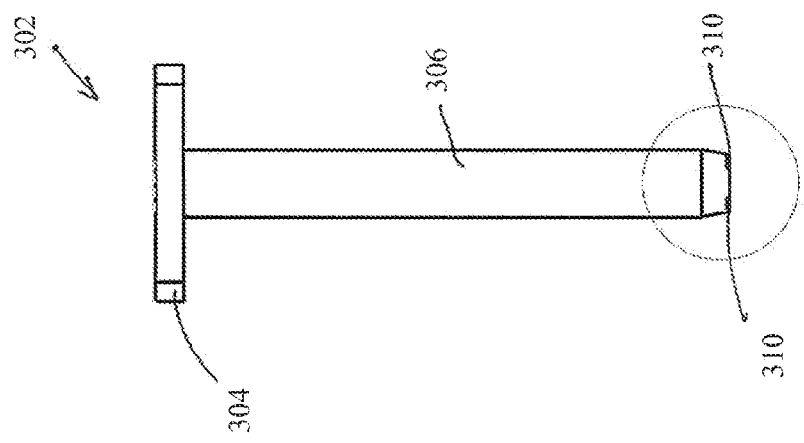

METHODS AND APPARATUSES FOR SHAPING CARTILAGE FOR TYMPANOPLASTY

RELATED APPLICATION

The present application claims the benefit of U.S. Provisional Application No. 61/576,451 filed Dec. 16, 2011, which is incorporated herein in its entirety by reference.

FIELD OF THE INVENTION

The present invention relates to devices for reconstruction of the tympanic membrane. More specifically, the present invention relates to devices for harvesting and shaping cartilage for use in tympanoplasty.

BACKGROUND OF THE INVENTION

Tympanoplasty is a surgical operation performed for the reconstruction of the ear drum, also known as the tympanic membrane. The most common indication for tympanoplasty are tympanic membrane perforations. The tympanic membrane can become perforated through a number of ways, including middle ear infections, external auditory canal infections, blunt trauma and iatrogenic causes. Although some tympanic membrane perforations can heal on their own, often surgery is necessary to repair the damage. Typically, a large tympanic membrane perforation is treated by inserting a graft into the ear adjacent the perforation. Various graft materials have been used for tympanoplasty, including fascia, perichondrium, vein tissue, dura, skin and cartilage.

Cartilage grafts have become popular due to cartilage being more rigid and resistive to absorption, having good long-term survival and being nourished largely by diffusion. In a typical cartilage tympanoplasty procedure, cartilage is harvested from the patient's ear, such as from the tragus, the cymba choncae or the choncal bowel. Then various techniques can be employed by the surgeon to manually shape the cartilage graft prior to implantation. The standard implantation procedure for larger perforations is known as medial grafting and involves placing the graft material beneath or medial to the original tympanic membrane. Small perforations can often be repaired by inserting a graft directly into the perforation.

Various products are available for thinning cartilage to an appropriate thickness (typically between 0.3 mm and 0.5 mm) for implantation. However, the final shape of the graft is manually determined by the surgeon. This "eyeballing" technique of shaping the graft is time consuming and can result in an imprecisely shaped graft that will not properly anchor adjacent the tympanic membrane. As such, it would be desirable for a device to provide simple and accurate shaping of cartilage grafts for tympanoplasty.

SUMMARY OF THE INVENTION

A single system can be used to harvest cartilage, trim the thickness of the cartilage and shape the cartilage for use in tympanoplasty. The system includes a punch and a template. Punch can include a handle and a plurality of interchangeable cutters having differently shaped cutting portions. Punch can be used with a first cutting portion to harvest cartilage. Template includes a top template that can include a pass through recess near a first end and a pair of thinning recesses on opposing sides near a second end and a bottom template that can include four cartilage wells each adjacent one end of the template on one of the bottom or top side. Harvested cartilage can be captured between top template and bottom template and cooperating thinning recesses and cartilage wells can be used to trim the cartilage to a desired thickness. Punch can then be fitted with a second cutter having a desired shape, which can be inserted through the pass through recess in top template to contact the cartilage in cartilage well to punch out the desired shape in the cartilage.

A method for harvesting and shaping cartilage for use in tympanoplasty uses a punch and a template. The punch is first used with a first cutting portion to harvest a cartilage graft from the patient. The graft is then sandwiched between a thinning recess of a top template portion and a cartilage well of a bottom template portion and a cutting device is used to thin the cartilage to a desired thickness. After the cartilage has been thinned to a desired thickness, the top template can be rotated relative to the bottom template to align a pass through recess of the top template with the cartilage well of the bottom template. A second cutting portion of a desired shape is attached to punch and is inserted through the pass through recess in top template to punch out the desired shape in the cartilage in the cartilage well.

In another embodiment, a single device can be used for harvesting and shaping cartilage for patching small perforations in the tympanic membrane. The device includes a cartilage punch and a punch body. Punch body includes a handle connected to a hollow elongate tube including a pair of cutting slits in a distal end of the tube. Plunger includes a knob connected to an elongate shaft that can be inserted into the tube of punch body. In use, a punch body of a desired diameter is used to harvest cartilage from a patient and the plunger is used to eject all but a desired thickness of cartilage from the tube. The excess cartilage is trimmed from the device with a cutting tool that is also subsequently inserted into the cutting slits in the side of the punch body to shape the cartilage. The shaped cartilage graft is then ejected from the punch body and can be used to patch a small perforation in the tympanic membrane.

The above summary of the various embodiments of the invention is not intended to describe each illustrated embodiment or every implementation of the invention. This summary represents a simplified overview of certain aspects of the invention to facilitate a basic understanding of the invention and is not intended to identify key or critical elements of the invention or delineate the scope of the invention.

BRIEF DESCRIPTION OF THE DRAWINGS

The invention may be more completely understood in consideration of the following detailed description of various embodiments of the invention in connection with the accompanying drawings, in which:

FIG. 1A is a perspective view of a device for harvesting and shaping cartilage for use in tympanoplasty according to an embodiment of the present invention.

FIG. 1B is a cross-sectional view of the device of FIG. 1A.

FIG. 2A is a side view of a handle of a punch for a device for harvesting and shaping cartilage for use in tympanoplasty according to an embodiment of the present invention.

FIG. 2B is an end view of the handle of FIG. 2A.

FIG. 2C is a perspective view of a cutter of a punch for a device for harvesting and shaping cartilage for use in tympanoplasty according to an embodiment of the present invention.

FIG. 2D is an end view of the cutter of the device of FIG. 2C.

FIG. 2E is a side view of the cutter of the device of FIG. 2C.

FIG. 4A is a perspective view of a bottom template of a device for harvesting and shaping cartilage for use in tympanoplasty according to an embodiment of the present invention.

FIG. 4B is a top view of the bottom template of FIG. 4A.

FIG. 4C is a side view of the bottom template of FIG. 4A.

FIG. 4D is a partial side view of the bottom template of FIG. 4A.

FIG. 5A is a side view of a punch body of a cartilage punch according to an embodiment of the present invention.

FIG. 5B is an end view of the punch body of FIG. 5A.

FIG. 5C is a partial view of the punch body of FIG. 5A.

Figure 2G:
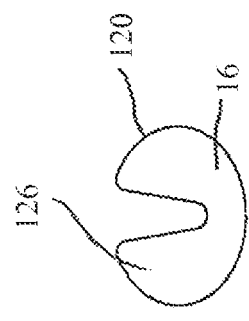
FIG. 2G is an end view of a cutter according to an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE DRAWINGS

In the following detailed description of the present invention, numerous specific details are set forth in order to provide a thorough understanding of the present invention. However, one skilled in the art will recognize that the present invention may be practiced without these specific details. In other instances, well-known methods, procedures, and components have not been described in detail so as to not unnecessarily obscure aspects of the present invention.

As can be seen in FIGS. 1A and 1B, a device 10 for harvesting and shaping cartilage grafts for use in tympanoplasty can include a punch 100 and a template 200. Punch 100 can first be used to harvest cartilage from a patient. In one embodiment, the harvested cartilage is choncal cartilage. Punch 100 can then be used in conjunction with template to shape the cartilage for implantation. In one embodiment, template 200 can be comprised of a clear acrylic material that allows for visualization of the cartilage as it is cut and shaped.

Referring now to FIGS. 2A-2E, punch 100 can include a handle 110 and a cutter 120. Handle 110 can be configured as a shaft 112 that can include a contoured portion 114 to facilitate gripping and manipulation of handle 110. Handle 110 can also include an insertion aperture 116 for an interchangeable cutter 120 to handle 110. Cutter 120 can include a shaft 122 for insertion into aperture 116 of handle 110 and a body 124. Body 124 can include a cutting portion 126 having a shape matching a desired shape of cartilage to be cut or harvested. In one embodiment, cutting portion is ¼ inch long.

Figure 2F:
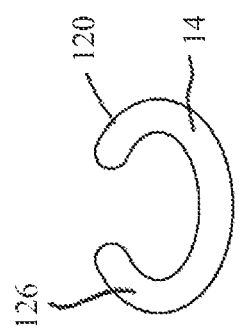
FIG. 2F is an end view of a cutter according to an embodiment of the present invention.

In use, shaft 122 of cutter 120 is inserted into insertion aperture 116 of handle 110. Shaft 122 of cutter 120 and insertion aperture 116 of handle 110 can include complementary keyed features 115, 121 to selectively lock and unlock cutter 120 and handle 110. Punch 100 can be provided with a single handle 110 and a plurality of cutters 120 having variously shaped cutting portions 126 that can be selectively used with handle 110 as desired. Various shapes can be used, including the "choncal cutter" shape 12 of FIG. 2D, the "crescent moon" shape 14 of FIG. 2F and the "cartilage shield" shape 16 of FIG. 2G. In one embodiment, cutting portions 126 are integrally formed with cutter 120. In another embodiment, cutting portions 126 can be separately formed from, for example, thin walled stainless steel rolled into the desired shaped, and pressed into appropriately shaped grooves in cutter 120. In one embodiment, the harvested cartilage is approximately 12 millimeters by 8.5 millimeters.

Figure 3B:
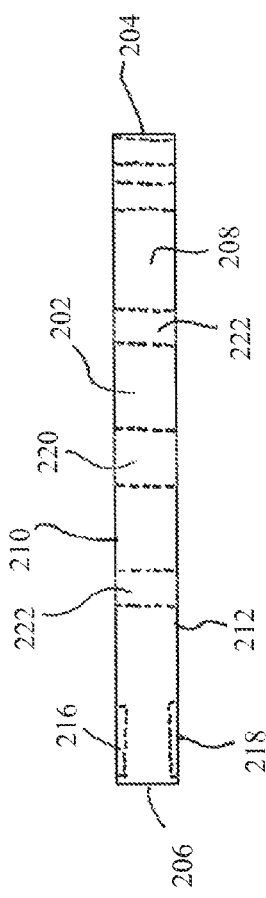
FIG. 3B is a top view of the top template of FIG. 3A.
Figure 3C:
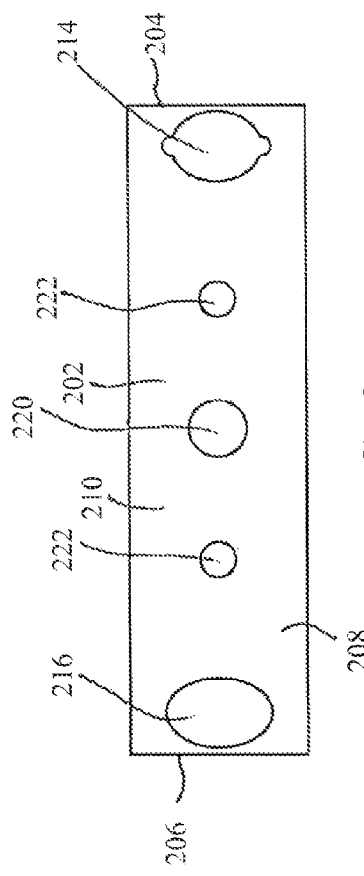
FIG. 3C is a side view of the top template of FIG. 3A.
Figure 3A:
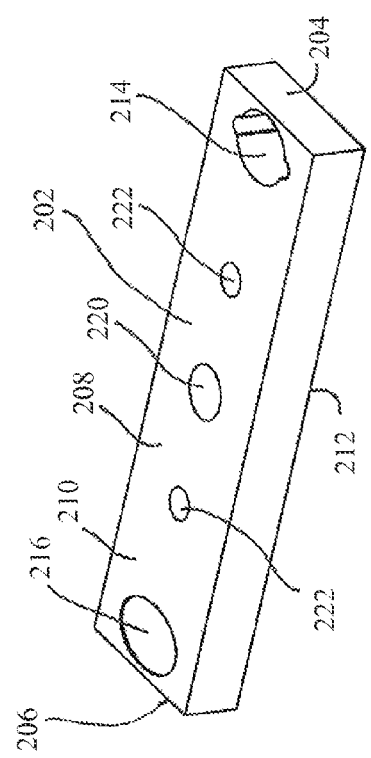
FIG. 3A is a perspective view of a top template of a device for harvesting and shaping cartilage for use in tympanoplasty according to an embodiment of the present invention.

Referring now to FIGS. 3A-3C, a top template portion 202 of template 200 is depicted. Top template 202 defines a first end 204 and second end 206 with a body 208 having a top surface 210 and a bottom surface 212 extending there between. Adjacent first end 204, top template 202 includes a pass through recess 214 extending through the entire thickness of top template 202 and abutting the end 204. A first thinning recess 216 is disposed on top surface 210 adjacent second end 206 and a second thinning recess 218 is disposed on bottom surface 212 adjacent second end 206. Each thinning recess 216, 218 can have a different depth to allow for thinning of cartilage to different thicknesses. Pass through recess 214 and first 216 and second 218 thinning recesses can all have a shape matching the shape of the body 124 of the cutter 120 of punch 100. In one embodiment, first thinning recess 216 is 0.3 millimeters deep and second thinning recess 218 is 0.5 millimeters deep. Top template 202 can also include a central aperture 220 and a pair of peg apertures 222, each of which extend through the entire thickness of top template 202. In one embodiment, the central aperture 220 is unthreaded.

A bottom template portion 252 of template is 200 is depicted in FIGS. 4A-4D. Bottom template 252 defines a first end 254 and second end 256 with a body 258 having a top surface 260 and a bottom surface 262 extending there between. Bottom template 252 can include four cartilage wells. A first cartilage well 264 is disposed adjacent first end 254 on top surface 260, a second cartilage well 266 is disposed adjacent second end 256 on top surface 260 and third 268 and fourth 270 cartilage wells are disposed on bottom surface 262 opposite of first 264 and second 266 cartilage wells, respectively. Each cartilage well 264, 266, 268, 270, can have a different depth to provide for shaving cartridge to different thicknesses. In one embodiment, the cartilage wells have thicknesses of 0.2 millimeters, 0.3 millimeters, 0.5 millimeters and 0.6 millimeters. Bottom template 252 can also include a lip 272 adjacent each cartilage well that defines a recessed surface 274 in top surface 260 and bottom surface 262 in which cartilage wells sit. Bottom template 252 can further include a central aperture 276 extending through body 258 and a pair of peg recesses 278 that can extend only partially through body 258. Peg recesses 278 can be disposed on both top surface 260 and bottom surface 262. In one embodiment, central aperture 276 is threaded.

In operation, initially a cutter 120 of a desired shape is selected and attached to handle 110 to form punch 100 for harvesting cartilage from the patient. Preferably, cartilage is "punched out" in the pattern shown in FIG. 2D. The cartilage graft can then be placed in one of the cartilage wells 264, 266, 268, 270 of bottom template 252, for example cartilage well 266. With cartilage graft in place, top template 202 can be connected to bottom template 252. This can be done by inserting fixation pegs 224 or other fasteners through peg apertures 222 in top template 202 and into peg recesses 278 of bottom template 252. A wing nut 251 can also be inserted through unthreaded central aperture 220 of top template 202 and threaded into threaded central aperture 276 of bottom template 252.

With the cartilage graft now captured between the top template 202 and the bottom template 252, the cartilage can be thinned to a desired thickness. This can be accomplished by inserting a thin profiled cutting tool, such as a razor, into the gap formed between the bottom surface 212 of the top template 202 and the recessed surface 274 of the bottom template 252. This shaves off the cartilage extending out of the cartilage well 266 and/or thinning recess and leaves cartilage of the desired thickness in the well 266 and/or recess. The fixation pegs 224 prevent torque on the templates 202, 252 during the cutting process. Cartilage can also be thinned in multiple steps, for example, making a first pass with the razor with the cartilage sandwiched between cartilage well 266 and first thinning recess 216 of top template 202, then turning top template 202 over and capturing cartilage between a second thinning recess 218 having a smaller depth than first thinning recess 216 and cartilage well 266. The excess cartilage can then be removed, so that only cartilage of the desired thickness remains. It should be noted that although this embodiment is described as forming a gap between the templates due to a recessed surface 274 on bottom template 252, either or both templates can include such recessed surfaces for forming a gap for thinning the cartilage.

Once the desired thickness of cartilage has been cut, a specific desired shape of the cartilage can be punched from the graft material in the cartilage well 266. A cutter 120 having a cutting portion 126 with a desired shape, such as the crescent moon shape 14 depicted in FIG. 2F, can be connected to handle 110. In other embodiments, cutter can have a full moon or cartilage shield shape 16, a ¾ moon shape or a ½ moon shape. To position the template 200 to punch a desired shape from the graft material, the top template 202 is pivoted around wing nut 251 relative to bottom template 252. Wing nut 251 can be slightly unscrewed so that fixation pegs 224 can be removed from peg recesses 278 in bottom template 252. Top template 202 can be rotated about its central aperture 220, which is unthreaded, to position pass through aperture 214 over the cartilage well 266 containing the graft material and then the wing nut 251 can be retightened and the fixation pegs 224 inserted back into the peg recesses 278 of bottom template 252. The pass through aperture 214 allows the cutter 120 of punch 110 to be passed through the top template 202 and into the cartilage well 266 of the bottom template 252. The cutter 120 presses the cartilage against the bottom of the well 266 and punches out the desired shape. In one embodiment, the pass through aperture 214 is the identical side and shape of the outer perimeter of the body 124 of cutter 120.

The final result is a precisely shaped and sized cartilage graft that can subsequently be used in a tympanoplasty operation. In one embodiment, the cartilage remains attached to residual underlying perichondrium that retains the initially harvested shape and dimension, which can be 12.5 millimeters by 8.5 millimeters, to allow the perichondrium to overlap the entire tympanic membrane. The periochondrium can then be anchored to the residual tympanic membrane and malleus in the medial underlay fashion as is known in the art to secure the thinned and shaped cartilage in the desired position. The device of the present invention thus provides for precise sizing and shaping of cartilage grafts that cannot be obtained with the devices of the prior art.

Referring now to FIGS. 5A-5C and 6, the elements of a cartilage punch according to an embodiment of the present invention are shown. Cartilage punch is designed to be primarily used with smaller tympanic membrane perforations than those with which the device 10 described above is used. Such smaller perforations do not require the precise shaping for larger perforations that overlay the entire tympanic membrane because they can be repaired by inserting cartilage directly into the perforation. Cartilage punch can be used to harvest and create inlay butterfly grafts to fill such smaller perforations.

Figure 6:
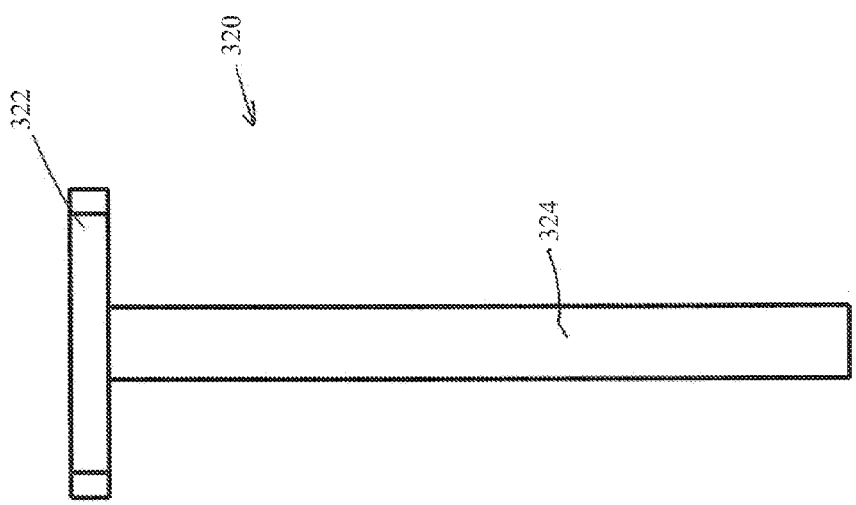
FIG. 6 is a side view of a plunger for a cartilage punch according to an embodiment of the present invention.

Cartilage punch includes a punch body 302, shown in FIGS. 5A-5C and a plunger 320, shown in FIG. 6. Punch body 302 includes a handle 304 connected to an elongate tube 306. Tube 306 can be hollow with an aperture 308 extending therethrough. At a distal end of tube 306, punch body 302 can include a pair of cutting slits 310 on opposing sides of tube 306. In one embodiment, tube 306 and aperture 308 have generally circular cross-sections. Plunger 320 includes a knob 322 connected to an elongate shaft 324. Shaft 324 of plunger 320 is sized and shaped to fit within aperture 308 through tube 306 of punch body 302.

In use, a punch body 302 of a desired size is used to harvest cartilage, such as conchal or tragal cartilage. The plunger 320 is then inserted into the aperture 308 through the punch body and can be used to push out all but a desired thickness of cartilage. Typically, the desired thickness of cartilage is 0.5 millimeters. The excess cartilage extending from the punch 300 can be trimmed off with a cutting device such as a scalpel. The cutting device can then be inserted into the cutting slits 310 in the side of the punch body 302 to shape the cartilage and the cartilage can then be ejected from the punch body 302 with the plunger 320.

Figure 8:
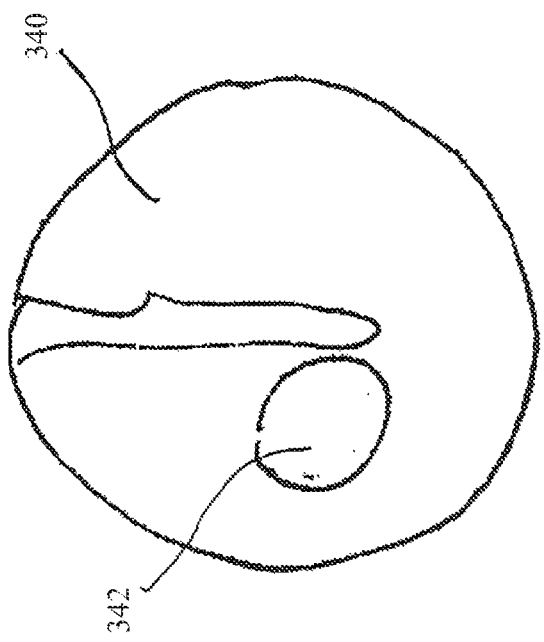
FIG. 8 is a schematic representation of a tympanic membrane with a perforation.
Figure 7A:
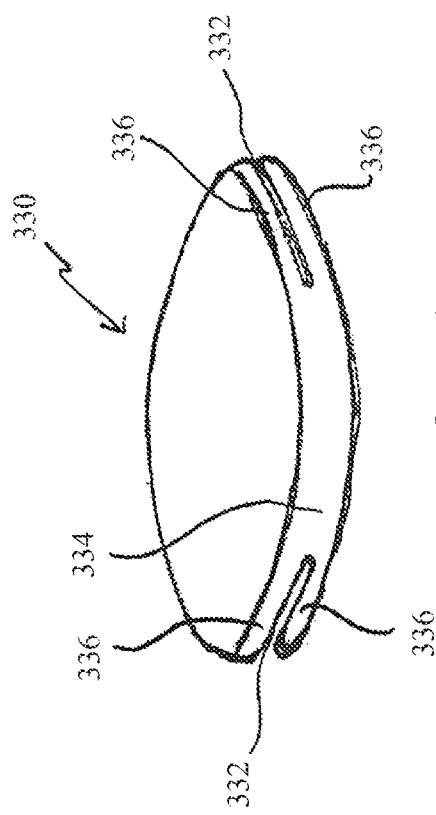
FIG. 7A is a perspective view of a cartilage graft according to an embodiment of the present invention.
Figure 7B:
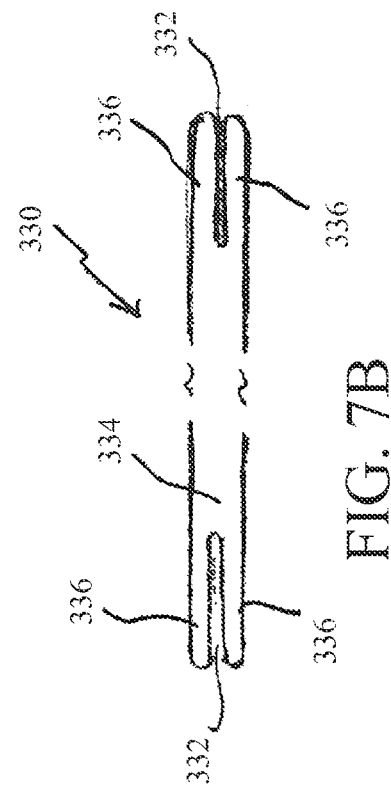
FIG. 7B is a side view of the cartilage graft of FIG. 7A.

The resulting cartilage graft 330 has a shape similar to that shown in FIGS. 7A and 7B. The graft includes slots 332 created through the cutting slits 310 in the punch 300, which create a narrower central portion 334 having the diameter of the perforation to be filled with overlaying "wings" 336. The graft can then be used to fill a small perforation 342 in the tympanic membrane 340, such as the perforation 342 shown in FIG. 8. The rim of the perforation 342 is first stripped to freshen the tissue at the perforation edge. The graft 330 is then pushed into the perforation 342, and is suspended about the tympanic membrane 340 by the wings 336 with the central portion 334 filling the perforation 342. In one embodiment, cartilage punches can be packaged in a kit having variously sized reusable punch bodies 302 and plungers 302. For example, a kit could include punches have diameters of 2.0, 3.0, 4.0 and 5.0 millimeters.

Various embodiments of systems, devices and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

The invention claimed is:

1. A system for harvesting and shaping cartilage for tympanoplasty, comprising:
   a first cutter adapted to harvest cartilage; and a template assembly including a cartilage well adapted to receive the harvested cartilage and a thinning opening adapted to allow the harvested cartilage to be thinned to a specific predefined thickness, the template assembly further including a pass-through recess operable with a second cutter to form the thinned cartilage into a specific predefined shape.

2. The system of claim 1, further comprising:
a cartilage punch adapted to interchangeably receive a plurality of cutters having differently shaped cutting portions including the first cutter operable with the cartilage punch to harvest the cartilage and the second cutter operable with the cartilage punch to form the harvested cartilage into the specific predefined shape; and
the template assembly further comprising:
a top template and a bottom template, the top template and bottom template connected to form the thinning opening therebetween to allow the harvested cartilage to be thinned to the specific predefined thickness, and wherein at least one of the top template and the bottom template includes the pass-through recess and the other of the top template and the bottom template includes the cartilage well adapted to be aligned with the pass-through recess.

3. The system of claim 2, wherein the cartilage punch includes a handle having a shaft, the shaft defining an insertion aperture shaped to selectively receive a cutter body of an interchangeable cutter.

4. The system of claim 3, wherein the cutter body includes a shaft, the shaft having keyed features that complement the insertion aperture to lock and unlock the cutter within the insertion aperture.

5. The system of claim 2, wherein the cutting portion of at least one of the cutters is removably attachable to a cutter body of the cutter.

6. The system of claim 2, wherein the other of the top template and bottom template includes a plurality of cartilage wells that are selectively alignable with the pass through recess.

7. The system of claim 6, wherein each cartilage well extends a different depth into the template.

8. The system of claim 2, wherein the thinning opening between the top template and bottom template is formed by a thinning recess in a surface on at least one of the top template and bottom template facing the other of the top template and bottom template.

9. The system of claim 8, wherein there are a plurality of thinning recesses and each thinning recess has a different depth.

10. The system of claim 9, wherein the thinning recesses are selectively alignable with the pass through recess.

11. The system of claim 2, the top template and bottom template each define a central aperture into which a peg can be inserted to hold the top template and bottom template together.

12. The system of claim 11, wherein the central aperture is threaded.

13. The system of claim 2, wherein the top template, the bottom template, or both can be comprised of a clear acrylic material.

14. The system of claim 2, wherein the shape of the pass-through recess matches a shape of a cutter body of at least one cutter.

15. A method of harvesting and shaping cartilage for tympanoplasty, comprising:
harvesting cartilage from a patient with a cartilage punch, the punch having a handle and a first cutter for harvesting the cartilage;
inserting the cartilage between a top template and a bottom template, the top template and bottom template defining a space therebetween;
inserting a cutting tool into the space between the top template and bottom template to form a thinned cartilage portion having a specific predefined thickness;
removing the first cutter from the punch and inserting a second cutter; and
inserting the second cutter through a pass through recess in one of the top template and the bottom template to shape the thinned cartilage portion into a specific predefined shape defined by the second cutter.

16. The method of claim 15, wherein inserting the cartilage between a top template and a bottom template includes sandwiching the cartilage between a thinning recess in one of the top template and bottom template and a cartilage well in the other of the top template and the bottom template, the thinning recess defining the space between the top template and the bottom template.

17. The method of claim 15, further comprising:
attaching the top and bottom template with a fastener and aligning the top template and bottom template in a first orientation for inserting the cutting tool to form the thinned cartilage portion;
following formation of the thinned cartilage portion, pivoting one of the top template and the bottom template about the fastener to align the top template and bottom template in a second orientation; and
wherein inserting the second cutter to shape the thinned cartilage portion into the specific predefined shape is done in the second orientation.

18. A system comprising:
means for harvesting cartilage from a patient;
means for holding the cartilage for thinning the cartilage to a specific predefined thickness; and
means for shaping the thinned cartilage into a specific predefined shape.

19. The system of claim 18, wherein the means for harvesting cartilage from a patient and the means for shaping the thinned cartilage into a specific predefined shape are interchangeably useable with a common handle.

20. The system of claim 18, wherein the means for holding the cartilage for thinning the cartilage also holds the cartilage for shaping with the means for shaping.

* * * * *